(12) United States Patent
Carreiro et al.

(10) Patent No.: US 7,236,252 B1
(45) Date of Patent: *Jun. 26, 2007

(54) SYSTEM AND APPARATUS FOR MEASURING DISPLACEMENTS IN ELECTRO-ACTIVE MATERIALS

(75) Inventors: Louis G. Carreiro, Westport, MA (US); Lawrence J. Reinhart, Wilmington, MA (US)

(73) Assignee: The United States of America as repersented by the Secretary of the Navy, Washington, DC (US)

( * ) Notice: Subject to any disclaimer, the term of this patent is extended or adjusted under 35 U.S.C. 154(b) by 385 days.

This patent is subject to a terminal disclaimer.

(21) Appl. No.: 10/914,776

(22) Filed: Aug. 5, 2004

(51) Int. Cl.
*G01B 11/02* (2006.01)
*G01B 13/08* (2006.01)
*G01B 7/16* (2006.01)
*G01N 33/00* (2006.01)

(52) U.S. Cl. .................. 356/498; 73/37.5; 73/763; 73/866

(58) Field of Classification Search ........... 356/485, 356/486, 487, 492, 493, 496, 498; 73/37.5, 73/763, 800, 866
See application file for complete search history.

(56) References Cited

U.S. PATENT DOCUMENTS

| | | | |
|---|---|---|---|
| 3,938,889 A * | 2/1976 | McKinnis | 356/498 |
| 4,436,419 A * | 3/1984 | Stetson et al. | 356/486 |
| 4,572,670 A * | 2/1986 | Fredrickson | 356/496 |
| 4,678,905 A * | 7/1987 | Phillips | 250/227.21 |
| 4,897,541 A * | 1/1990 | Phillips | 250/227.21 |
| 5,381,299 A * | 1/1995 | Provenzano et al. | 73/718 |
| 5,446,546 A | 8/1995 | Breidenbach et al. | |
| 5,633,467 A | 5/1997 | Paulson | |
| 5,915,267 A * | 6/1999 | Kim | 73/1.15 |
| 6,053,035 A | 4/2000 | Nomura et al. | |
| 6,457,359 B1 | 10/2002 | Suzuki | |
| 6,563,570 B1 | 5/2003 | Okada | |
| 6,584,857 B1 | 7/2003 | Furlani et al. | |
| 6,604,266 B1 * | 8/2003 | Tajima et al. | 29/25.35 |
| 6,637,265 B1 * | 10/2003 | Hay et al. | 73/433 |
| 6,718,832 B1 * | 4/2004 | Hay et al. | 73/790 |
| 6,860,136 B1 * | 3/2005 | Hay et al. | 73/437 |

* cited by examiner

*Primary Examiner*—Gregory J. Toatley, Jr.
*Assistant Examiner*—Patrick Connolly
(74) *Attorney, Agent, or Firm*—James M. Kasischke; Jean-Paul A. Nasser; Michael P. Stanley

(57) ABSTRACT

A device designed to apply uniaxial pressure to the surface of an electro-active material while simultaneously applying a current to the material under controlled temperature conditions and then measuring the displacement of the material by means of a laser interferometer. The device involves a housing with a chamber in which a sample of material is secured. The chamber has an aperture with a quartz window that allows the laser beam from the interferometer to pass. The sample is connected to electrodes and the chamber is filled with dielectric oil that applies the uniaxial pressure to one side of the sample. The device is placed onto a thermal control system. When the appropriate thermal and pressure conditions are established, current is applied to the sample and the interferometer measures the displacement.

13 Claims, 2 Drawing Sheets

SYSTEM AND APPARATUS FOR MEASURING DISPLACEMENTS IN ELECTRO-ACTIVE MATERIALS

STATEMENT OF GOVERNMENT INTEREST

The invention described herein may be manufactured and used by or for the Government of the United States of America for governmental purposes without the payment of any royalties thereon or therefore.

CROSS REFERENCE TO OTHER RELATED APPLICATIONS

This patent application is co-pending with a related patent application Ser. No. 10/914,777 entitled AN IMPROVED SYSTEM AND APPARATUS FOR MEASURING DISPLACEMENTS IN ELECTRO-ACTIVE MATERIALS, by Louis G. Carreiro and Lawrence J. Reinhart both of whom are inventors as to this application.

BACKGROUND OF THE INVENTION (1) Field of the Invention

The present invention relates to a device for measuring displacements in a solid material, and more specifically to a device for applying uniaxial hydraulic pressure to the surface of an electro-active material while at the same time permitting a light source to be focused on the same surface in order to perform interferometric non-contact displacement measurements of the material under controlled conditions of pressure, temperature and applied voltage.

(2) Description of the Prior Art

The active elements of most sonar transducers consist of rings, disks or plates fabricated with electro-active (piezoelectric and electrostrictive) ceramics such as lead zirconium titanate (PZT) and with emerging materials such as the solid solution of lead magnesium niobate and lead titanate (PMN-PT). In a common configuration, these elements are bonded together with epoxy to form a stack that is then placed under a compressive load. When the stack is electrically driven, the applied compressive force opposes the tensile stress (internal strain) generated in the ceramic. This arrangement prevents the ceramic from going into tension and thus reduces the chance of failure due to fracturing.

Attempts to measure the electromechanical properties of stack elements often result in data that is difficult to interpret since the epoxy adhesive, metal electrodes and compression fixture tend to mask the properties of the ceramic. Therefore, a device for the direct characterization of the pre-stressed ceramic that eliminates the unwanted contributions from the stack assembly components is needed.

Currently, there exists a quasi-static apparatus used to determine the 33-mode properties of electro-active ceramics under simultaneous conditions of high electrical drive, electrical bias, compressive load and temperature.

With the above-mentioned quasi-static apparatus, a sample with dimensions of 2 mm×2 mm×10 mm. (an aspect ratio of 5:1 ensures 33-mode operation) is placed under a unidirectional compressive load along its length. The pre-stress is applied over a range of 0 to 10 ksi with a pneumatic piston designed to have low mechanical loss and low ac stiffness so that a "constant stress" boundary condition is met. The entire apparatus is placed onto a thermal control system in order to obtain data versus temperature. The sample is then electrically driven with a 10 Hz sine wave of the order of 2.0 Mv/m. The charge versus the applied field is measured using an integrating capacitor, and the longitudinal strain versus the field is measured with strain gauges attached to the sides of the sample. From these measurements, the large signal dielectric constant $\in_{33}^T$ the piezoelectric constant $d_{33}$, and the coupling factor, $k_{33}$, can be calculated as a function of drive signal, bias field, pre-stress and temperature. Young's modulus is obtained from the measurement of strain versus applied stress.

The device described above has several limitations. The required geometry and small sample size often cause problems with mechanical alignment, and under compressive load, samples are prone to mechanical cracking and electrical breakdown. Precise attachment of the strain gauges to the samples is difficult, affecting the reproducibility of the measurements from sample to sample. Furthermore, the gauges introduce stray capacitance, and due to their close proximity, exhibit electrical cross talk and promote electrical discharge arcing. Since temperature is controlled via an environmental chamber, long equilibration times are required before data can be acquired. In addition, temperature gradients within the chamber also affect the ability to repeat the measurements. For the most part, the prior art apparatus lacks the reliability and precision that is necessary to characterize electro-active ceramics in a reproducible and efficient manner. What is needed is a device capable of applying uniaxial hydraulic pressure to the surface of an electro-active material while at the same time performing non-contact displacement measurements of the material under controlled conditions of pressure, temperature and applied voltage.

SUMMARY OF THE INVENTION

It is a general purpose and object of the present invention to provide a means of measuring displacement in electro-active material under applied voltage through the application of a uniaxial constant force without the use of strain gauges.

It is a further object to provide a means of measuring displacement in electro-active material through a non-contact means such as laser interferometry.

Another object is to provide a means for measuring displacement in electro-active material that will not subject samples of the material to mechanical cracking and electrical breakdown.

Still another object is to provide a means for measuring displacement in electro-active material that will ensure reproducibility of the measurements from sample to sample.

These objects are accomplished with the present invention through the use of a high pressure optical cell, essentially a testing chamber with an optical aperture capable of containing a sample of electro-active material and subjecting it to high levels of hydraulic pressure, in conjunction with a laser interferometer system and thermal control system. The cell allows non-contact interferometric displacement measurements of electro-active (piezoelectric and electrostrictive) materials to be performed under controlled conditions of pressure, temperature and applied voltage.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings wherein.

DESCRIPTION OF THE PREFERRED EMBODIMENT

Figure 1:
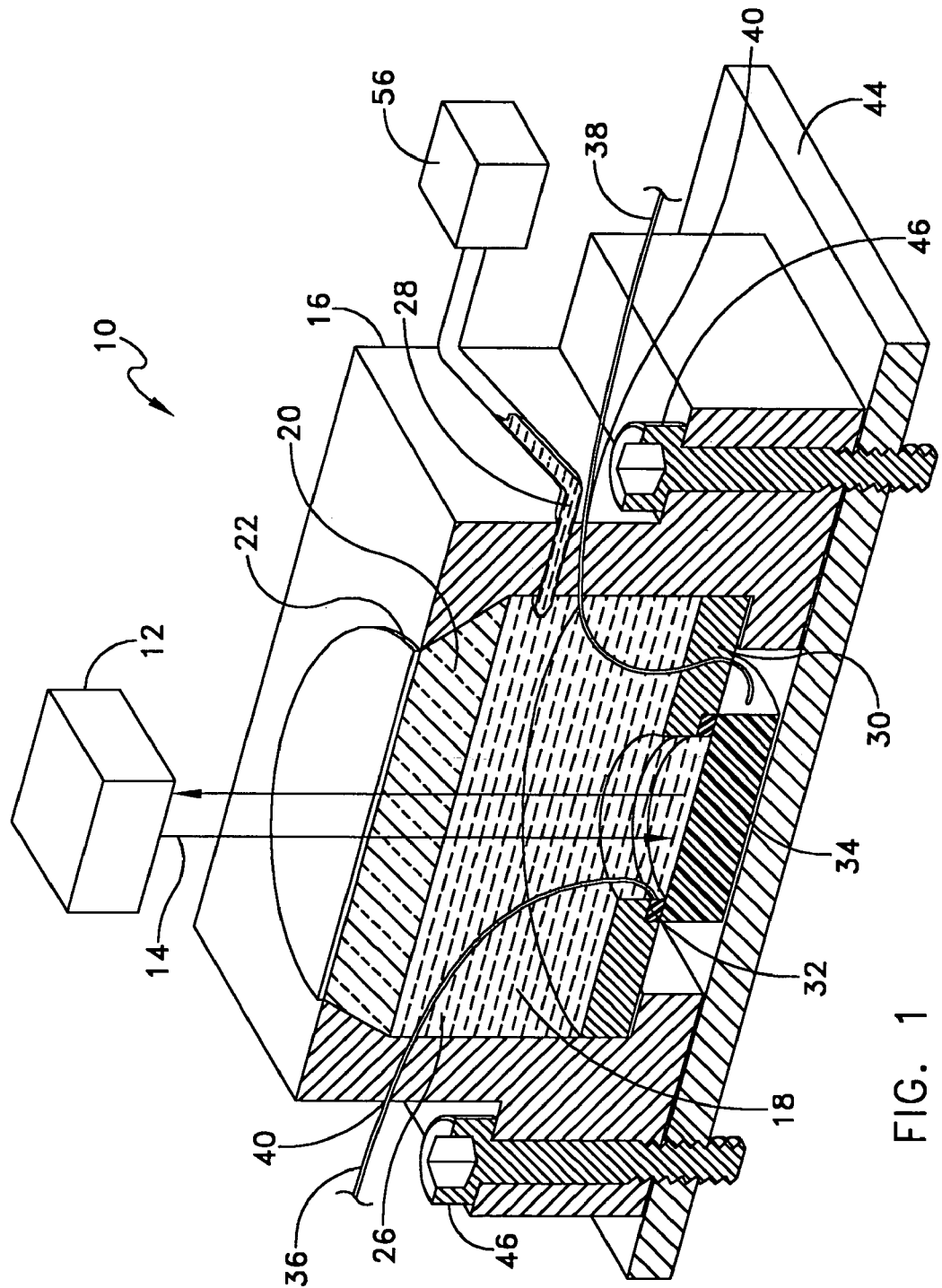
FIG. 1 shows a cross section of the high pressure optical cell in conjunction with an interferometer.

Referring now to FIG. 1 there is shown a high pressure optical cell 10 in use with a laser interferometer 12. Laser interferometer 12 is configured for a single beam 14. In the preferred embodiment, the cell 10 consists of a stainless steel cell body 16, however, it is to be understood that the present device is not limited to that particular metal and could be made of titanium or other materials. The cell 10 houses a cavity 18 with a single quartz glass window 20 that is transparent to laser radiation of a particular wavelength. In the preferred embodiment, the wavelength is $\lambda=632$ nm, but is not limited as such. It is to be understood that the present device is not limited to the use of quartz glass for the window 20 and could be made of other optically transparent materials, providing said materials are transparent to the laser radiation in use. The window 20 has an anti-reflective coating 22 on its surface transparent to light of the same wavelength as the laser beam 14 to prevent multiple reflections in the cavity 18 that might give rise to false signals to the interferometer detector 12. The window 20 can also be beveled to allow the internal pressure to seal the quartz glass against the cell body 16 thus insuring a hermetic seal.

Figure 2:
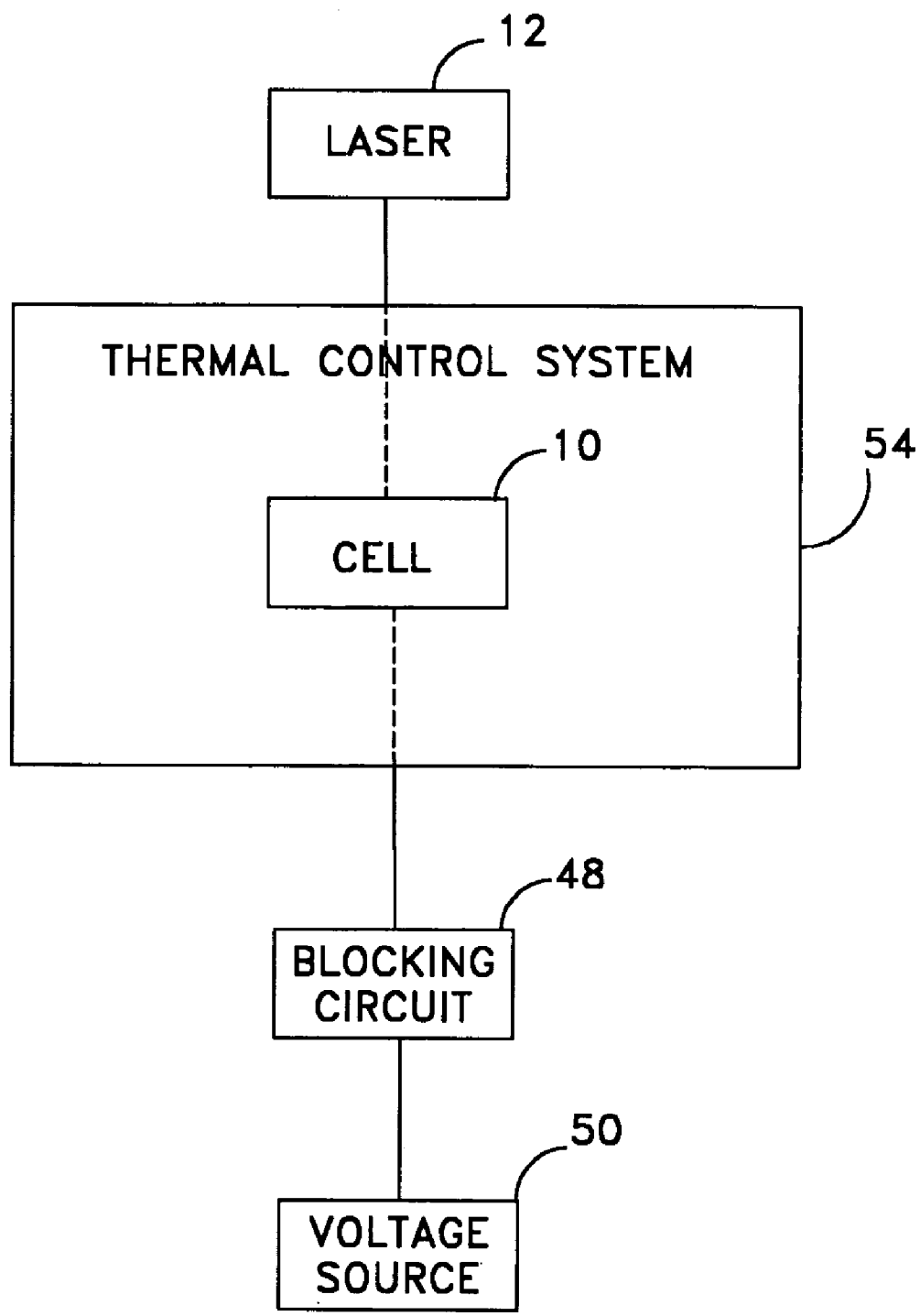
FIG. 2 shows a block diagram of the system components comprising the high pressure optical cell in use with a voltage source, blocking circuit, laser interferometer and thermal control system.

The cavity 18 is filled with a high dielectric oil 26 with a matching index of refraction to that of the quartz window 20. The high dielectric oil 26 is introduced into the cavity 18 through the liquid pressure inlet/outlet port 28 of the cell body 16 from a pressure pump control system 56 that generates and controls hydraulic pressure. A cylindrical compression seal 30 with a rubber gasket 32 fits inside the cavity 18 in a piston like manner onto a specimen 34 of electro-active material. The increasing liquid pressure in the cavity 18 seals the perimeter of the specimen 34. This sealing process provides a uniaxial constant force over the entire surface of the specimen 34 thus minimizing edge effects. Electrical contact is accomplished with wire leads 36 and 38 that are soldered to the specimen 34 and then passed through small openings 40 in the cell body 16, which are then sealed with epoxy. The electrical connections are made from the cell body 16 via leads 36 and 38 to a blocking circuit 48 and high voltage power supply 50 as illustrated in FIG. 2. In the preferred embodiment, a vacuum chuck base plate 44 holds the specimen 34 in place, however, it is to be understood that the present device is not limited to that particular means of holding the specimen 34 in place. The cell body 16 is secured to the plate 44 by torque bolts 46. The entire fixture comprising the cell body 16, specimen 34 and plate 44 is placed onto a thermal control system 54 as shown in FIG. 2 in order to control the temperature of the sample.

The cell 10 is designed to measure the displacement of electro-active materials under uniaxial pressure loads in high-voltage electric fields. In the preferred embodiment, the cell body 16 accommodates a specimen 34 with cross-sectional area ranging from 0.25 to 1.0 in$^2$ and thickness ranging from 0.1 to 0.25 inches. It is to be understood, however, that the present device is not to be limited by the size of the specimen 34 that it can accommodate. The specimen 34 is placed on base plate 44 positioned directly beneath rubber gasket 32 of the compression seal 30. Wire leads 36 and 38 are soldered to the specimen 34. The torque bolts 46 are then tightened at a specified torque. The cavity 18 of the cell 10 is flooded with the high-dielectric oil 26 while allowing air to bleed from the system. The cavity 18 is pressurized to the desired level. The cell 10 and attached plate 44 are then placed onto the thermal control system 54 to achieve a desired temperature. The cell body 16 and attached plate 44 are then mounted onto a three-way high precision optical stage (not shown), with tilt and yaw capability, which is positioned in the beam path 14 of the laser interferometer 12. The cell 10 is optically aligned to the interferometer 12 to acquire data as high-voltage electric fields cause displacement in the electro-active specimen 34.

This invention has several distinct advantages over the prior art. The present invention utilizes a non-contact method that measures strain via a laser interferometer 12, unlike prior art methods that employs strain gauges physically attached to the specimen 34. This feature allows measurements to be performed with nanometer resolution. Unidirectional (uniaxial) pre-stresses of up to 20 ksi are applied using hydraulic fluid 18 rather than mechanical compression. Since the ends of the specimen 34 are not clamped (between the platens of a press) they are free to move, eliminating the need for geometries with fixed aspect ratios. The present invention offers a variable frequency range of 1.0 Hz to 20 kHz and is not limited to a single operating frequency. Since the laser beam 14 can be positioned anywhere on the surface of the specimen 34, homogeneity of the surface can be evaluated.

What has thus been described is a device for applying uniaxial hydraulic pressure to the surface of an electro-active material while at the same time permitting a light source to be focused on the same surface in order to perform non-contact interferometric displacement measurements of the material under controlled conditions of pressure, temperature and applied voltage.

Obviously many modifications and variations of the present invention may become apparent in light of the above teachings. For example the cell 10 may be made of various materials capable of withstanding high pressures. The dielectric fluid 18 can be any of a number of fluids. The optical aperture 20 may be made of any optically transparent material. The laser frequency of the interferometer can vary according to the type of measurements taken.

In light of the above, it is therefore understood that within the scope of the appended claims, the invention may be practiced otherwise than as specifically described.

What is claimed is:

1. An apparatus for measuring displacements in a specimen of a solid material, comprising:
   a means for applying controlled uniaxial pressure to the specimen of said material;
   a means for applying controlled thermal energy to said specimen;
   a means for applying an electric field to said specimen; and
   a means for applying radiant light to a surface of said specimen to measure the displacement of the surface upon the application of said electric field.

2. An apparatus according to claim 1 wherein said means for applying controlled pressure to a specimen of said material further comprises:
   a housing surrounding a cavity in which said specimen is placed;
   a dielectric fluid hermetically contained at a variable pressure within said cavity, said dielectric fluid surrounding said specimen; and a means for controllably maintaining said cavity with a desired pressure of said dielectric fluid.

3. An apparatus according to claim 2 wherein said means for controllably maintaining said cavity with a desired pressure of said dielectric fluid comprises a hydraulic pump.

4. An apparatus according to claim 1 wherein said means for applying controlled thermal energy to said specimen comprises a thermal control system.

5. An apparatus according to claim 1 wherein said means for applying an electric field to said specimen further comprises:
 a high-voltage power supply; and
 two wire leads capable of conducting electric current in electrical contact with said specimen and connected to said high-voltage power supply.

6. An apparatus according to claim 1 wherein said means for applying radiant light to a surface of said specimen to measure the displacement of the surface upon the application of said electric field comprises a laser interferometer directing a laser beam at the specimen.

7. An apparatus for measuring displacements in a solid material, comprising:
 a housing surrounding a cavity in which a specimen of said material is placed;
 a dielectric fluid hermetically contained at a variable pressure within said cavity;
 a means for controllably maintaining said cavity with a desired pressure of said dielectric fluid;
 a high-voltage power supply;
 two wire leads capable of conducting electric current in electrical contact with said specimen and connected to said high-voltage power supply for applying an electric field to said specimen;
 a means for applying controlled thermal energy to said specimen; and
 an aperture within said housing transparent to light to allow a laser beam from a laser interferometer to be directed at the specimen to measure the displacement of a surface of said specimen upon the application of an electric field to said specimen.

8. An apparatus according to claim 7 wherein said aperture within said housing transparent to light is a quartz window.

9. An apparatus according to claim 8 wherein said quartz window has an anti-reflecting coating.

10. An apparatus according to claim 8 wherein said quartz window has the same index of refraction as said dielectric fluid.

11. An apparatus according to claim 7 wherein said means for controllably maintaining said cavity with a desired pressure of said dielectric fluid comprises a hydraulic pump.

12. An apparatus according to claim 8 wherein said means for applying controlled thermal energy to said specimen comprises a thermal control system.

13. An apparatus according to claim 7 wherein said material is an electro-active material.

* * * * *